United States Patent
Chun

(10) Patent No.: US 8,303,541 B2
(45) Date of Patent: Nov. 6, 2012

(54) PROTECTIVE GUARD FOR NEEDLES OF INJECTION DEVICES HAVING REMOVABLE NEEDLE ASSEMBLIES

(76) Inventor: Thomas Chun, Northridge, CA (US)

( * ) Notice: Subject to any disclaimer, the term of this patent is extended or adjusted under 35 U.S.C. 154(b) by 237 days.

(21) Appl. No.: 12/822,699

(22) Filed: Jun. 24, 2010

(65) Prior Publication Data
US 2011/0319832 A1 Dec. 29, 2011

(51) Int. Cl.
*A61M 5/00* (2006.01)
(52) U.S. Cl. .......... 604/110; 604/198; 604/263
(58) Field of Classification Search .......... 604/110, 604/198, 263
See application file for complete search history.

(56) References Cited

U.S. PATENT DOCUMENTS

| | | | | |
|---|---|---|---|---|
| 4,923,447 | A * | 5/1990 | Morgan | 604/198 |
| 4,927,414 | A * | 5/1990 | Kulli | 604/110 |
| 5,137,521 | A * | 8/1992 | Wilkins | 604/198 |
| 5,279,579 | A * | 1/1994 | D'Amico | 604/192 |
| 5,411,487 | A * | 5/1995 | Castagna | 604/198 |
| 5,472,430 | A * | 12/1995 | Vaillancourt et al. | 604/198 |
| 5,573,513 | A * | 11/1996 | Wozencroft | 604/198 |
| 5,591,138 | A * | 1/1997 | Vaillancourt | 604/263 |
| 5,695,475 | A * | 12/1997 | Best et al. | 604/198 |
| 6,162,197 | A * | 12/2000 | Mohammad | 604/195 |
| 6,183,445 | B1 * | 2/2001 | Lund et al. | 604/198 |
| 6,183,446 | B1 * | 2/2001 | Jeanbourquin | 604/198 |
| 6,325,781 | B1 * | 12/2001 | Takagi et al. | 604/198 |
| 6,416,497 | B1 * | 7/2002 | Kirk | 604/198 |
| D476,419 | S * | 6/2003 | Swenson | D24/130 |
| 6,669,671 | B1 * | 12/2003 | Mohammad | 604/195 |
| 6,926,696 | B2 * | 8/2005 | Mohammed | 604/195 |
| 7,211,065 | B2 * | 5/2007 | Miller | 604/110 |
| 7,727,190 | B2 * | 6/2010 | Miller | 604/110 |
| 7,955,310 | B2 * | 6/2011 | Hirota et al. | 604/263 |
| 8,062,252 | B2 * | 11/2011 | Alheidt et al. | 604/110 |
| 8,062,265 | B2 * | 11/2011 | Millerd | 604/192 |
| 2007/0078408 | A1 * | 4/2007 | Wang | 604/198 |
| 2008/0167611 | A1 * | 7/2008 | Miller | 604/110 |

* cited by examiner

*Primary Examiner* — Nicholas Lucchesi
*Assistant Examiner* — Scott Medway
(74) *Attorney, Agent, or Firm* — James A. Italia; Italia IP

(57) ABSTRACT

Protection for the otherwise exposed sharp point of a needle of an injection device. A two part cover for the needle comprises a stationary base which engages the injection device, and a relatively movable cover. The cover is guided to slide longitudinally along the base by a groove-and-projection system. The projection is held in an initial position, and slides along the groove during injection. At the end of the injection, the projection is immobilized in the groove at a final position, and immobilizes the moveable cover in a deployed position covering the needle.

5 Claims, 4 Drawing Sheets

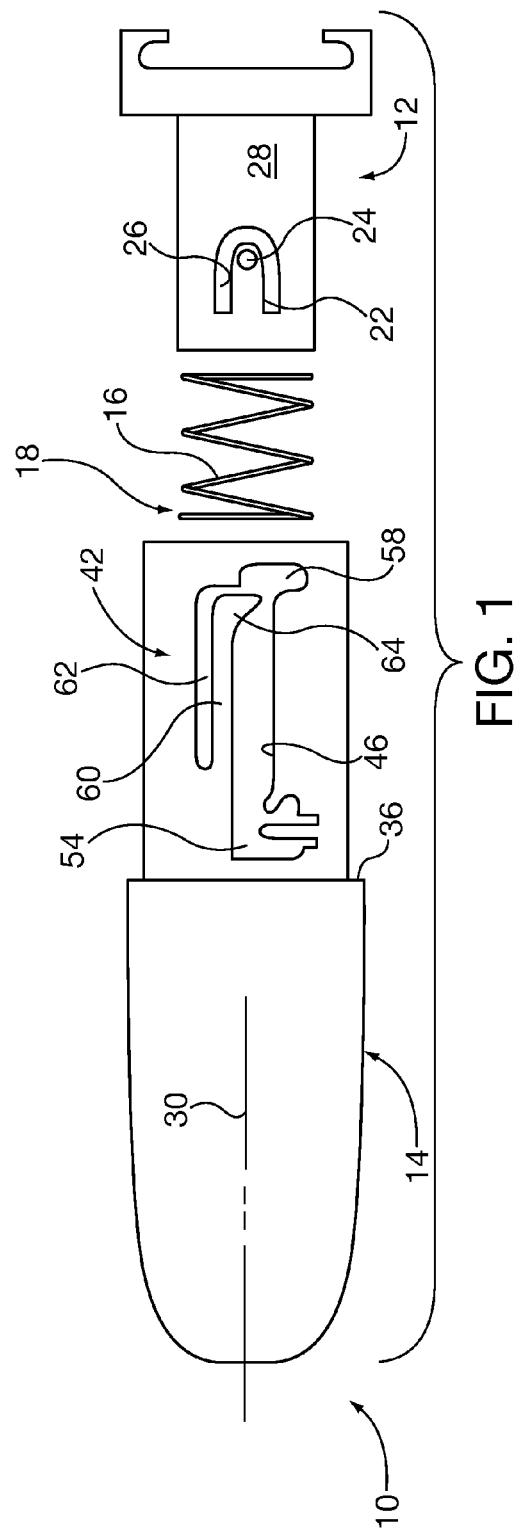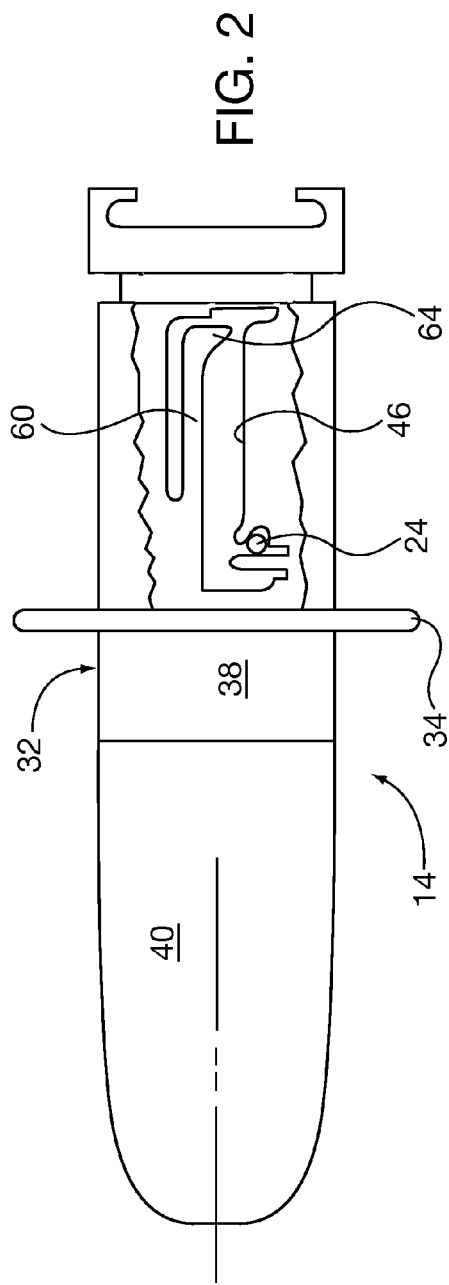

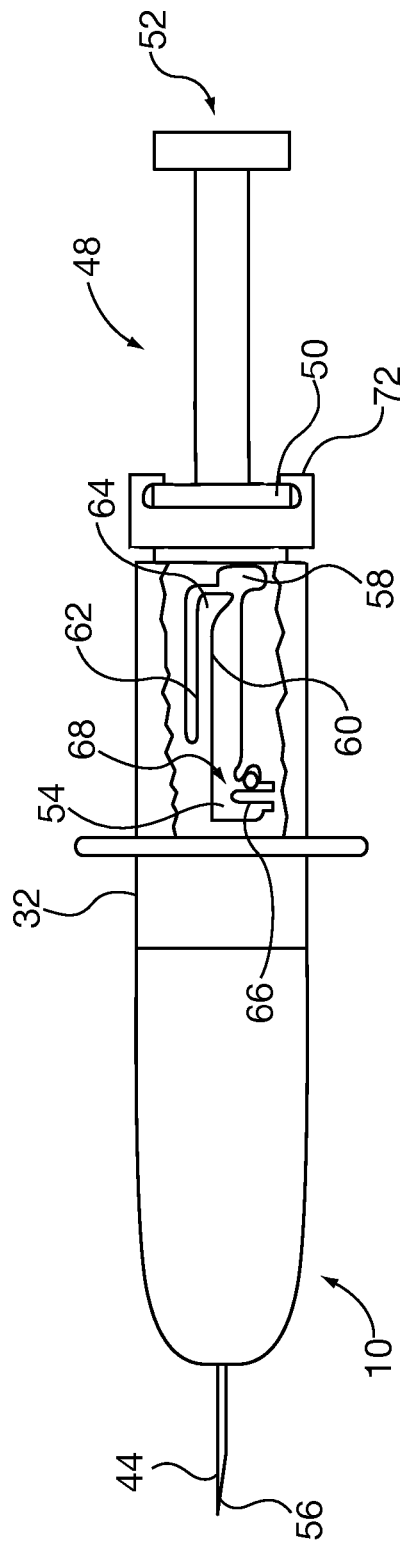
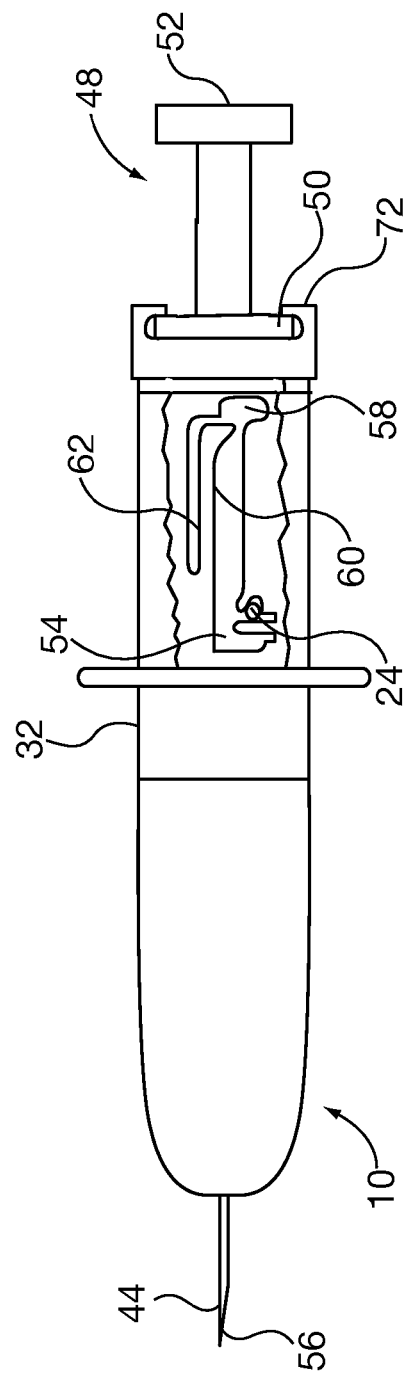
FIG. 3
FIG. 4

PROTECTIVE GUARD FOR NEEDLES OF INJECTION DEVICES HAVING REMOVABLE NEEDLE ASSEMBLIES

FIELD OF THE INVENTION

The present invention pertains to injection devices such as syringes and autoinjectors, and more particularly to a guard arrangement which covers sharp points of injection devices.

BACKGROUND OF THE INVENTION

Syringes, autoinjectors, and like injection devices have long been used to deliver medicaments and other substances transdermally. An injection device typically has a reservoir for storing a liquid to be injected, a plunger to pressurize the stored liquid, and an elongated slender pointed needle for penetrating skin and other tissues, so as to deliver the pressurized liquid into the body.

Because the point is very sharp, it easily penetrates human tissues, clothing, protective gear such as rubber gloves, and other articles. This presents a hazard to medical personnel due to unintended pricking of the personnel's body. This can be uncomfortable, can cause the personnel to drop or otherwise mishandle equipment, and most of all, threatens to transfer contaminants from an injected person's blood to the medical personnel.

Countermeasures directed to unintended pricking of the body have been proposed. However, many countermeasures introduce annoying drawbacks. For example, a cover may need to be manually installed and manually removed when needed. This may for example oblige medical personnel to put down other equipment and objects and perform the necessary installation or removal, or otherwise interfere with expeditious performance of medical tasks.

There remains a need for an uncomplicated yet effective protective device for preventing unintended pricking due to exposed needles, or "sharps", as they have become informally known, which is self-deploying and which makes minimal demands on

SUMMARY

The present invention addresses the above concern by providing a self-deploying cover assembly for exposed needles and the like. The self-deploying cover or protective guard may be a self-contained device which is installable to the needle assembly of an injection device such as a syringe or autoinjector having a separately installable needle assembly.

The overall function of the guide structure is to immobilize the injection device in an initial or "ready" position, and to subsequently lock a protective sleeve or cover over the needle at the conclusion of the injection. The structure of the protective guard may include two complementing parts, one of which is secured to the injector device and may be regarded as being stationary relative to the injector device, the other part being movable relative to the stationary part. The operative principle includes a guide structure, for example comprising a guiding groove formed in a first part, and a projection which is formed in a relatively movable second part, and which rides within the groove. The guide structure may be formed in one of the first and second parts, and the projection may be formed in the other of the first and second parts. As the injection proceeds, the projection rides in the groove as the first and second parts move relative to one another.

The groove is configured to include a first receptacle which holds the projection until manual force moves the second part such that the projection forces its way out of the first receptacle. Travel of the second part and its projection towards the patient being injected brings the projection to a point enabling maximal projection of the needle from the injection device. When the injection is finished, the needle may be retracted, with the second part of the self-deploying cover following passively as the needle retracts, but latching into a final position which latches the protective sleeve over the needle point so that direct access to the needle point is prevented.

A spring provides force to move the second part as described. Movement of the second part relative to the first under influence of this spring causes the protective device to be self-deploying in that once installed, the user need take no affirmative action to assure that the protective sleeve be moved to a deployed position covering the needle point at the conclusion of injecting.

A supplementary cover which surrounds the second part and covers the exterior surface of the second part is preferably provided. The supplementary cover may provide an outwardly projecting flange for providing convenient support for the fingers of the person administering the injection.

A significant advantage of the present invention is that the novel self-deploying protective cover enables medicaments to be provided with needle assemblies which may then be installed in the barrel of the syringe. The syringe and its associated plunger may be reused, which limits the structure which must be renewed after each injection to the needle assembly and its associated fluid reservoir. Alternatively stated, it is not necessary to utilize and discard an entire injection device after each injection. The injection device which may enjoy the benefits of replacement of needle assembly only is protected against inadvertent pricks by the novel self-deploying protective cover.

The novel self-deploying protective cover may be made available as a modular adjunct or accessory to the injection device, so that not only are the barrel and plunger of the injection device retained for subsequent usages, but so is the self-deploying protective cover.

It is an object of the invention to provide improved elements and arrangements thereof by apparatus for the purposes described which is inexpensive, dependable, and fully effective in accomplishing its intended purposes.

These and other objects of the present invention will become readily apparent upon further review of the following specification and drawings.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein:

FIG. 1 is an exploded side view of elements of the self-deploying protective cover of the present invention.

FIG. 2 is a side view of the components of FIG. 1 shown assembled.

FIG. 3 is a side view of the components of FIG. 1 assembled over an injection device, showing the plunger of the injection device as it would be immediately prior to an injection.

FIG. 4 is a side view similar to FIG. 3, but showing the plunger mostly but not fully depressed.

DETAILED DESCRIPTION

Figure 5:
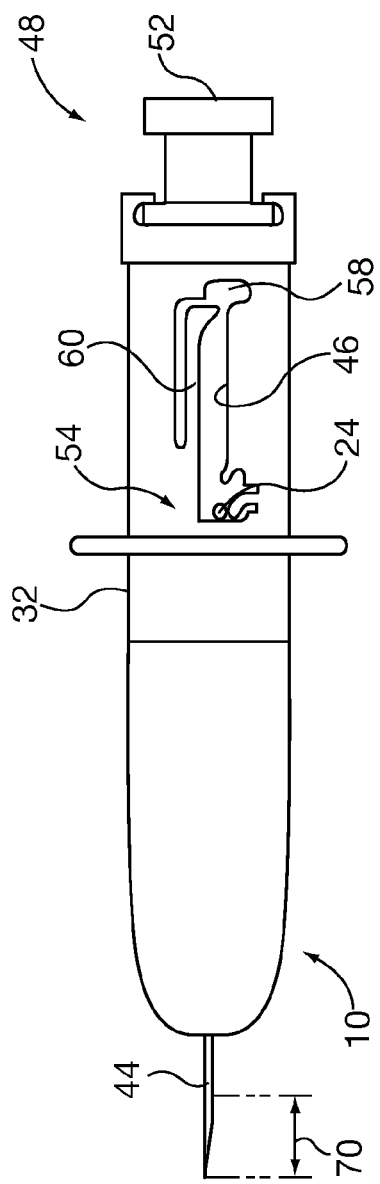
FIG. 5 is a side view similar to FIG. 4, but showing the plunger fully depressed.

Referring first to FIG. 1, according to at least one aspect of the invention there is shown components of a self-deploying protective cover 10, without its associated injection device 12 (which will be seen in FIG. 3). The self-deploying cover 10 may comprise a base 12, a protective sleeve 14, and a coil spring 16. The protective sleeve 14 may have an open interior 18 adapted to interfit telescopingly with the base 12. That is, the open interior 18 may be dimensioned and configured to slidably receive the base 12 in close cooperation therewith.

The base 12 is seen to have a finger 22 bearing a projection 24. The finger 22 is defined by a U-shaped channel 26 formed in the wall 28 of the base 12. The projection 24 projects outwardly from the finger 22. Projection in the outward direction will be understood to be away from the axis 30 of the protective sleeve 14. The axis 30 is coincident with the longitudinal axis of the needle of the injection device (see FIG. 3). For example, if formed as part of a self-deploying protective cover which is fabricated to scale for use with a typical syringe or autoinjector, such as the syringe shown in FIG. 3, the projection 24 may rise above the surrounding surfaces by a magnitude of perhaps one thirty-second or one sixteenth of an inch.

Of course, in other implementations of the invention, a protective sleeve corresponding to the protective sleeve 14 may be received within a base corresponding to the base 12.

Figure 8:
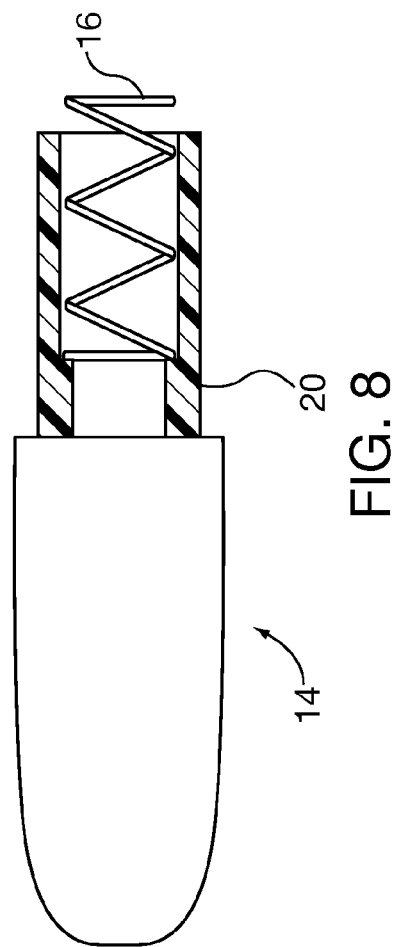
FIG. 8 is a partly cross sectional side detail view of a component seen at the left of FIG. 1.

Turning momentarily to FIG. 8, the protective sleeve 14 may have an internal shoulder 20 adapted to generate a seat or reaction surface for the spring 16. The base 12 may have a corresponding shoulder (not shown, but similar in construction to the shoulder 20) so that the spring 16 may urge the base 12 away from the protective sleeve 14.

FIG. 2 shows the components of FIG. 1 united or assembled. Also, a new component is introduced in FIG. 2, namely, an outer sleeve 32 which is disposed to slip over the protective sleeve 14 along part of the length thereof. The outer sleeve 32 may have an outwardly projecting flange 34 for engaging the finger or fingers of a user when the user is grasping an injection device to be used with the self-deploying cover 10. For the purposes of this invention, the term "finger" may encompass the thumb.

The protective sleeve 14 may comprise an external circumferential shoulder 36 (best seen in FIG. 1) disposed to limit axial travel of the outer sleeve 32 along the protective sleeve 14. As seen in FIG. 2, the outer surface 38 of the outer sleeve 32 may be coextensive with the outer surface portion 40 of the protective sleeve 14, so when the protective sleeve 14 and the outer sleeve 32 are assembled, the respective outer surfaces 38, 40 are flush.

Figure 7:
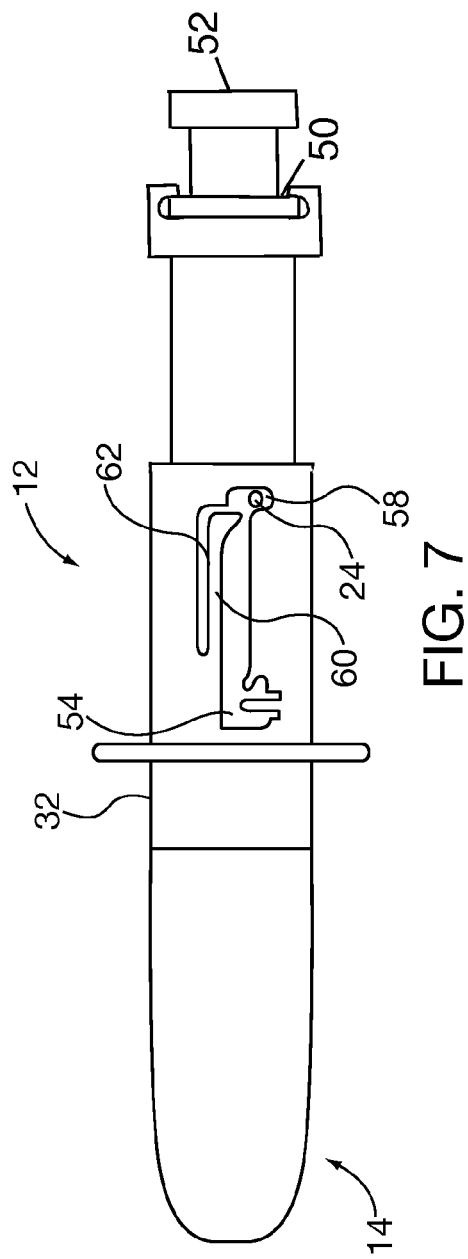
FIG. 7 is a side view similar to FIG. 6, but showing the protective cover latched into the deployed position covering the retracted needle.

The self-deploying protective cover 10 has a guide feature to facilitate moving the protective sleeve 14 between a deployed position covering the needle of the injection device (as seen in FIG. 7) and a retracted position exposing the needle for administering injections (as seen in FIG. 3).

Again referring to FIG. 1, the protective sleeve 14 comprises a groove 42 of somewhat complex configuration, which serves primarily to define a path of travel of the projection 24 as the protective sleeve 14 moves between the retracted position of FIG. 3, which exposes the needle 44, and the deployed position of FIG. 7. These motions are in directions parallel to and in coaxial relation to the longitudinal axis 30.

The groove 42 comprises a principal channel 46 which is occupied by the projection 24 throughout most of the motion of the projection 24 during operation of the self-deploying cover 10. Other channels formed in the groove 42 generally provide lesser support functions other than guiding the projection 24 along the longitudinal axis 30. The lesser structural features of the groove 42 will be described hereinafter.

During motion of the projection 24 and hence between the base 12 and the protective cover 14, and also referring to FIG. 3, the base 12 engages an injection device such as a syringe 48 having a needle assembly including the needle 44, a barrel (of which only a flange 50 is visible), and a plunger 52. The plunger 52 is adapted to fit into and slidably along the barrel so as to engage and impose pressure on the removable needle assembly, thereby driving fluid to be injected through the needle 44 as injection proceeds. The needle assembly may be conventional, and is used with some syringes so that needle assemblies only need be renewed, the barrel 50 and plunger 52 being reusable. In the assembled condition shown in FIG. 3, the base 12 engages the barrel of the syringe 48, thus providing a stable platform relative to which the protective sleeve 14 may move. Interaction of the projection 24 and the groove 42 causes the base 12 to guide the protective sleeve 14 as the protective sleeve 14 moves between the deployed position and the retracted position.

Engagement of the barrel by the base 12 is improved by an engagement element 72 which is disposed to engage and retain the outwardly projecting flange 50 of the barrel of the syringe 48. The engagement element resiliently fits to and partially surrounds the flange 50.

The principal channel 46 is dimensioned and configured to receive the projection 24 in close cooperation therewith. The principal channel 46 may have an initial terminal 54 located proximate the point 56 of the needle 44 and a final terminal 58 located proximate the plunger 52. The principal channel 46 is parallel to the longitudinal axis 30.

A deflectable arm 60 is formed in the groove 46, being defined between the principal channel 46 and a relief channel 62, the entire purpose of which is to contribute to defining the deflectable arm 60. The deflectable arm 60 terminates in an enlarged head 64 which is configured to restrict the open area of the principal channel 46. Ordinarily, the enlarged head 64 obstructs the principal channel 46 to casual or unintended travel of the projection 24. However, under manual pressure imposed by depressing the plunger 52 as for an injection, the deflectable arm 60 deflects by moving laterally by the projection 24, thereby enabling the projection 24 to move along the principal channel 46 towards the final terminal 58. It may be said then that the enlarged head 58 of the deflectable arm 60 yieldingly closes the principal channel 46. This creates a one-way gate which immobilizes the projection 24 and hence the protective sleeve 14 in the deployed position covering the point 56 of the needle 44, as will be further described hereinafter.

Returning to FIG. 2, the initial position of the self-deploying cover 10 on the syringe 48 is shown. The groove 42 is seen to comprise a retention element which communicates to the principal channel 46 and is disposed to retain the projection 24 in the retracted position immediately prior to commencing an injection. The retention element is disposed between the initial terminal 54 and the final terminal 58, and more particularly is located proximate the initial terminal 54. In the retracted position seen in FIG. 3, the needle 44 and its point 56 are exposed and may be inserted into the patient.

The retention element comprises a short deflectable retention arm 66 which retains the projection 24 in a short retention channel 68. Once the plunger 52 is fully depressed and the shot has been administered, the continued pressure on the plunger 52 affects the barrel and base 12 assembly, and more specifically the projection 24 to ride in a cam-like manner on the surface formed in the short arm 66, and after being released from engagement with the short arm 66, responsively moves circumferentially to the principal channel 46. From this point, and responsively to the further depression of the plunger 52 (and the further compression of the spring 16), the projection 24 moves first towards the initial terminal 54 and subsequently towards the final terminal 58. Frictional characteristics of the interfit of the base 12, the protective sleeve 14, the barrel of the syringe 48, and the needle assembly bearing the needle 44, and spring characteristics of the spring 16, which is disposed to urge the protective sleeve 16 into the deployed position relative to the base 12, assure that the protective sleeve 14 will move relative to the base 12 as described. The needle assembly may be a conventional needle assembly which is separate from the rest of the syringe 48.

After the movement of the plunger 52 and barrel assembly (illustrated in FIG. 4) is sufficient to dislodge the projection 24 from the short channel 68, by displacing the short arm 66 as shown in FIG. 5, continued depression of the plunger 52 will ultimately force the projection 24 to occupy the initial terminal 54. The needle 44 may be projected additionally by such continued depression, as indicated by a dimension arrow 70 in FIG. 5.

Figure 6:
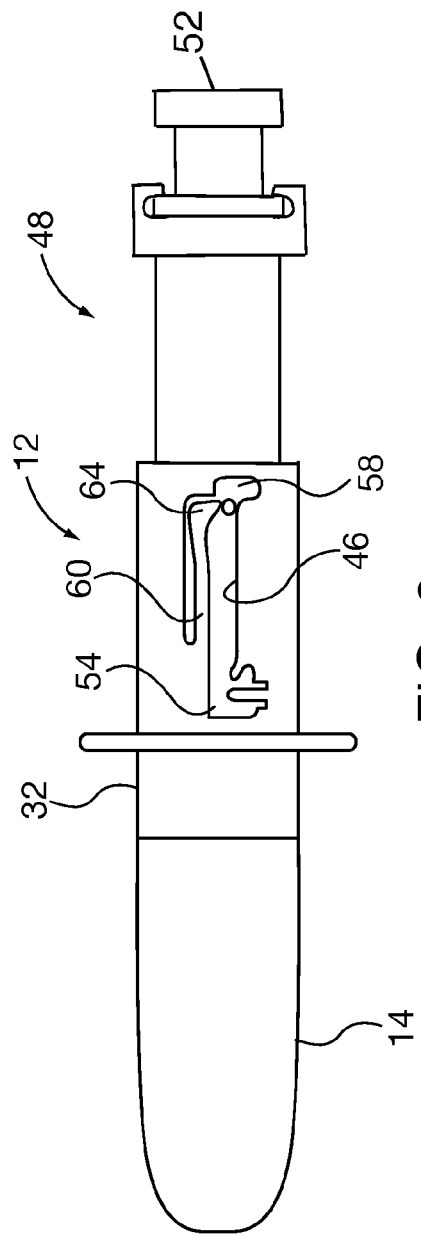
FIG. 6 is a side view similar to FIG. 5, but showing the needle retracted into the protective cover, the point no longer exposed.

Turning now to FIG. 6, release of pressure on the plunger 52 will enable the spring 16 (not visible in FIG. 6) to urge the base 12 apart from the protective sleeve 14. This causes the base 12 and barrel assembly (along with the plunger 52 contained within the barrel) to move to the right as seen in FIG. 6, thereby retracting the needle 44 attached to said barrel, which is no longer visible in FIG. 6 because it has retracted into the protective sleeve 14.

It will be seen that as the projection 24 rides within the principal channel 46 from the initial terminal 54 of the principal channel 46 to approach the final terminal 58, it passes the enlarged head 64 of the deflectable arm 60, thereby causing the deflectable arm 60 to deflect. Deflection allows the projection 24 to pass the enlarged head 64. The deflectable arm 60 then returns to its normal position, as shown in FIG. 5 for example. As best seen in FIG. 7, return of the deflectable arm 60 opposes return of the projection 24 in an opposite direction after passing the deflectable arm 60, thereby entrapping the projection 24 at the final terminal 58 of the principal channel 46. The projection 24 and hence the protective sleeve are thus secured in the deployed position.

In one implementation, the invention may be regarded as a self-deploying protective cover such as that utilizing the protective sleeve 10, the base 12, and the spring 16. Optionally, the invention may be regarded as a self-protective cover of the type described above, further comprising the outer sleeve 32.

In another implementation, the invention may be regarded as an injection device such as the syringe 48, improved by further comprising a self-deploying protective cover for covering the sharp point of the needle of the injection device.

The present invention is susceptible to modifications and variations which may be introduced thereto without departing from the inventive concepts. For example, action of deflectable members such as the deflectable arms and may be modified such that the displacement occurs in a radial direction relative to the axis of the needle of the injection device, such as the needle. Where such modification is practiced, elements such as the supplementary cover may be modified to accommodate outward deflection while still performing their intended functions. Also, relative locations of the groove and the projection may be exchanged between the protective cover and the base if desired.

While the present invention has been described in connection with what is considered the most practical and preferred embodiment, it is to be understood that the present invention is not to be limited to the disclosed arrangements, but is intended to cover various arrangements which are included within the spirit and scope of the broadest possible interpretation of the appended claims so as to encompass all modifications and equivalent arrangements which are possible.

I claim:

1. An injection device provided with a needle having a sharp point and a self-deploying protective cover for covering the sharp point of the needle, comprising:
   an injection portion comprising
      a barrel having an outwardly projecting flange,
      a removable needle assembly adapted to fit into and slidably along the barrel, and
      a plunger adapted to fit into and slidably along the barrel so as to engage the removable needle assembly and impose pressure on the removable needle assembly, thereby driving fluid to be injected through the needle as injection proceeds; and
   a self-deploying protective cover for covering the sharp point of the needle of the injection portion, comprising:
      a protective sleeve which is movable to a deployed position covering the needle of the injection device and to a retracted position exposing the needle for administering injections, wherein the protective sleeve has a longitudinal axis which is coincident with the longitudinal axis of the needle of the injection device and an outwardly projecting projection;
      a base disposed to engage the injection device and guide the protective sleeve as the protective sleeve moves between the deployed position and the retracted position in directions parallel to and in coaxial relation to the longitudinal axis of the needle, wherein the base has formed therein a groove having a principal channel which is dimensioned and configured to receive the projection of the protective sleeve therein, has an initial terminal located proximate the point of the needle and a final terminal located proximate the plunger of the injection device, is parallel to the longitudinal axis of the needle, comprises a deflectable arm disposed to yieldingly obstruct the principal channel, comprises a retention element communicating to the principal channel and disposed to retain the projection of the protective sleeve in the retracted position; and comprises a spring disposed to urge the protective sleeve into the deployed position relative to the base, wherein
   the retention element is disposed to release the projection into the principal channel of the groove when the plunger of the injection device is depressed in a direction effecting an injection, and wherein the retention element comprises a retention channel and a deflectable retention arm disposed to hold the projection in the retention channel immediately prior to commencing an injection,
   the spring is disposed to urge the protective sleeve into the deployed position when the plunger of the injection device is released, the projection rides in the principal channel of the groove and approaches the final terminal of the principal channel of the groove after the plunger of the injection device is released, the deflectable arm is disposed to enable the projection to pass thereby as the projection approaches the final terminal of the principal channel of the groove and to oppose return of the projection in an opposite direction after passing the deflectable arm, thereby entrapping the projection at the final terminal of the principal channel of the groove and securing the protective sleeve in the deployed position.

2. The self-deploying protective cover of claim 1, wherein the deflectable arm has an enlarged head and is disposed to move laterally by the projection when the protective sleeve moves along the principal channel towards the final terminal.

3. The self-deploying protective cover of claim 2, wherein the final terminal of the principal channel of the groove is yieldingly closed by the enlarged head of the deflectable arm.

4. An injection device provided with a needle having a sharp point and a self-deploying protective cover for covering the sharp point of the needle, comprising:

an injection portion comprising
  a barrel having an outwardly projecting flange,
  a removable needle assembly adapted to fit into and slidably along the barrel, and
  a plunger adapted to fit into and slidably along the barrel so as to engage the removable needle assembly and impose pressure on the removable needle assembly, thereby driving fluid to be injected through the needle as injection proceeds; and
a self-deploying protective cover for covering the sharp point of the needle of the injection portion, comprising:
  a protective sleeve which is movable to a deployed position covering the needle of the injection device and to a retracted position exposing the needle for administering injections, wherein the protective sleeve has a longitudinal axis which is coincident with the longitudinal axis of the needle of the injection device and an outwardly projecting projection;
  a base disposed to engage the injection device and guide the protective sleeve as the protective sleeve moves between the deployed position and the retracted position in directions parallel to and in coaxial relation to the longitudinal axis of the needle, wherein the base has formed therein a groove having a principal channel which is dimensioned and configured to receive the projection of the protective sleeve therein, has an initial terminal located proximate the point of the needle and a final terminal located proximate the plunger of the injection device, is parallel to the longitudinal axis of the needle, comprises a deflectable arm disposed to yieldingly obstruct the principal channel, comprises a retention element communicating to the principal channel and disposed to retain the projection of the protective sleeve in the retracted position; and comprises a spring disposed to urge the protective sleeve into the deployed position relative to the base, wherein
  the retention element is disposed to release the projection into the principal channel of the groove when the plunger of the injection device is depressed in a direction effecting an injection,
  the spring is disposed to urge the protective sleeve into the deployed position when the plunger of the injection device is released, the projection rides in the principal channel of the groove and approaches the final terminal of the principal channel of the groove after the plunger of the injection device is released, the deflectable arm is disposed to enable the projection to pass thereby as the projection approaches the final terminal of the principal channel of the groove and to oppose return of the projection in an opposite direction after passing the deflectable arm, thereby entrapping the projection at the final terminal of the principal channel of the groove and securing the protective sleeve in the deployed position;

further comprising an outer sleeve disposed to slip over the protective sleeve, and wherein the protective sleeve comprises an external circumferential shoulder disposed to limit axial travel of the outer sleeve along the protective sleeve, and further wherein the outer sleeve comprises an outwardly projecting flange for engaging the fingers of the user.

5. An injection device provided with a needle having a sharp point and a self-deploying protective cover for covering the sharp point of the needle, comprising:

an injection portion comprising
  a barrel having an outwardly projecting flange,
  a removable needle assembly adapted to fit into and slidably along the barrel, and
  a plunger adapted to fit into and slidably along the barrel so as to engage the removable needle assembly and impose pressure on the removable needle assembly, thereby driving fluid to be injected through the needle as injection proceeds; and
a self-deploying protective cover for covering the sharp point of the needle of the injection portion, comprising:
  a protective sleeve which is movable to a deployed position covering the needle of the injection device and to a retracted position exposing the needle for administering injections, wherein the protective sleeve has a longitudinal axis which is coincident with the longitudinal axis of the needle of the injection device and an outwardly projecting projection;
  a base disposed to engage the injection device and guide the protective sleeve as the protective sleeve moves between the deployed position and the retracted position in directions parallel to and in coaxial relation to the longitudinal axis of the needle, wherein the base has formed therein a groove having a principal channel which is dimensioned and configured to receive the projection of the protective sleeve therein, has an initial terminal located proximate the point of the needle and a final terminal located proximate the plunger of the injection device, is parallel to the longitudinal axis of the needle, comprises a deflectable arm disposed to yieldingly obstruct the principal channel, comprises a retention element communicating to the principal channel and disposed to retain the projection of the protective sleeve in the retracted position; and comprises a spring disposed to urge the protective sleeve into the deployed position relative to the base, wherein
  the retention element is disposed to release the projection into the principal channel of the groove when the plunger of the injection device is depressed in a direction effecting an injection,
  the spring is disposed to urge the protective sleeve into the deployed position when the plunger of the injection device is released, the projection rides in the principal channel of the groove and approaches the final terminal of the principal channel of the groove after the plunger of the injection device is released, the deflectable arm is disposed to enable the projection to pass thereby as the projection approaches the final terminal of the principal channel of the groove and to oppose return of the projection in an opposite direction after passing the deflectable arm, thereby entrapping the projection at the final terminal of the principal channel of the groove and securing the protective sleeve in the deployed position;

wherein the retention element is disposed between the initial terminal of the principal channel of the groove and the final terminal of the principal channel of the groove proximate the initial terminal of the principal channel of the groove, and further wherein the projection moves towards the initial terminal of the principal channel of the groove after being released into the groove responsively to the plunger of the injection device being depressed, and still further wherein the projection moves towards the final terminal of the principal channel of the groove after reaching the initial terminal of the principal channel of the groove prior to moving towards the final terminal of the principal channel of the groove.

* * * * *